United States Patent
Alterki

(10) Patent No.: US 9,739,787 B2
(45) Date of Patent: Aug. 22, 2017

(54) METHOD FOR DIAGNOSING SLEEP APNEA BY MEASURING ADIPSIN AND BETATROPHIN LEVELS

(71) Applicant: Abdulmohsen Ebrahim Alterki, Misherf (KW)

(72) Inventor: Abdulmohsen Ebrahim Alterki, Misherf (KW)

( * ) Notice: Subject to any disclaimer, the term of this patent is extended or adjusted under 35 U.S.C. 154(b) by 0 days.

(21) Appl. No.: 15/255,088

(22) Filed: Sep. 1, 2016

(65) Prior Publication Data

US 2017/0059587 A1    Mar. 2, 2017

Related U.S. Application Data

(60) Provisional application No. 62/213,075, filed on Sep. 1, 2015.

(51) Int. Cl.
| | |
|---|---|
| G01N 33/53 | (2006.01) |
| G01N 33/48 | (2006.01) |
| G01N 33/68 | (2006.01) |
| G01N 33/74 | (2006.01) |

(52) U.S. Cl.
CPC .. *G01N 33/6896* (2013.01); *C12Y 304/21046* (2013.01); *G01N 33/6869* (2013.01); *G01N 33/74* (2013.01); *G01N 2333/47* (2013.01); *G01N 2333/525* (2013.01); *G01N 2333/5437* (2013.01); *G01N 2333/575* (2013.01); *G01N 2333/58* (2013.01); *G01N 2333/96433* (2013.01); *G01N 2800/2864* (2013.01)

(58) Field of Classification Search
None
See application file for complete search history.

(56) References Cited

U.S. PATENT DOCUMENTS

| | | | |
|---|---|---|---|
| 7,901,885 | B2 | 3/2011 | Salonen et al. |
| 8,110,584 | B2 | 2/2012 | Mueller et al. |
| 2004/0002112 | A1 | 1/2004 | Mann et al. |
| 2010/0323379 | A1 | 12/2010 | Somers et al. |
| 2012/0116181 | A1 | 5/2012 | Richards et al. |

OTHER PUBLICATIONS

Barnum et al, 1984. Journal of Immunological Methods. 67(1934): 303-309.*
Derosa et al, 2013. Inflammation. 36(4): 914-920.*
Kader et al, 2005. Am J Gastroenterol. 100(2): 414-423 (pp. 1-24 as printed).*
Butler, M.G., et al., "Clinically Relevant Known and Candidate Genes for Obesity and their Overlap with Human Infertility and Reproduction," J. of Assit. Rep. and Genetics, 32(4): pp. 495-508 (2015).

* cited by examiner

*Primary Examiner* — Zachary Howard
(74) *Attorney, Agent, or Firm* — Richard C. Litman

(57) ABSTRACT

The method for diagnosing sleep apnea includes measuring concentrations of biomarkers in a patient's bodily sample. To determine whether a patient suffers from sleep apnea, or has a predisposition for developing sleep apnea, a sample from the patient is analyzed. If one or more of the following biomarker concentrations are found in the patient's sample, then the patient may be diagnosed as suffering from sleep apnea or having a predisposition for developing sleep apnea: between approximately 992.8 pg/mL and approximately 1309.6 pg/mL of adipsin; between approximately 1,640 pg/mL and approximately 2,900 pg/mL of betatrophin; between approximately 8,090.82 pg/mL and approximately 11,829.07 pg/mL of brain-derived neurotrophic factor (BDNF); between approximately 11.82 pg/mL and approximately 88.26 pg/mL of interleukin-13 (IL-13); between approximately 49.45 pg/mL and approximately 103.29 pg/mL of tumor necrosis factor-$\alpha$ (TNF-$\alpha$); and between approximately 16.55 pg/mL and approximately 29.76 pg/mL of the protein encoded by Human DNAJC27.

3 Claims, No Drawings

METHOD FOR DIAGNOSING SLEEP APNEA BY MEASURING ADIPSIN AND BETATROPHIN LEVELS

CROSS-REFERENCE TO RELATED APPLICATION

This application claims the benefit of U.S. Provisional Patent Application Ser. No. 62/213,075, filed on Sep. 1, 2015.

BACKGROUND OF THE INVENTION

1. Field of the Invention

The present invention relates to medical diagnostic techniques, and particularly to a method for diagnosing sleep apnea based on measuring concentrations of specific biomarkers in a biological sample from a patient.

2. Description of the Related Art

Sleep apnea is a sleep disorder characterized by pauses in breathing, or instances of shallow or infrequent breathing, during sleep. Each pause in breathing (referred to as an "apnea") can last for several seconds to several minutes, and may occur five or more times in an hour. There are three forms of sleep apnea: central sleep apnea (CSA), obstructive sleep apnea (OSA), and complex or mixed sleep apnea (i.e., a combination of central and obstructive) constituting 0.4%, 84%, and 15% of cases, respectively. In CSA, breathing is interrupted by a lack of respiratory effort, and in OSA, breathing is interrupted by a physical block to airflow despite respiratory effort, and snoring is common. According to the National Institutes of Health, 12 million Americans have OSA.

Regardless of the type of sleep apnea, an individual with sleep apnea is rarely aware of having difficulty breathing, even upon awakening. Sleep apnea is typically recognized as a problem by others witnessing the individual during episodes or is suspected because of its effects on the body (i.e., sequelae). Symptoms may be present for years (or even decades) without identification, during which time the sufferer may become conditioned to the daytime sleepiness and fatigue associated with significant levels of sleep disturbance. Sleep apnea affects not only adults but some children as well.

It has been shown that hypoxia (i.e., an inadequate supply of oxygen), which is one of the resultant characteristics of sleep apnea, promotes angiogenesis which increases vascular and tumor growth. This, in turn, results in a 4.8 times higher incidence of cancer mortality. Additionally, OSA has been shown to be further associated with numerous other health problems, such as obesity, diabetes and cardiovascular diseases.

Self-diagnosis of sleep apnea is extremely difficult and the standard medical testing technique for sleep apnea, polysomnography, is relatively cumbersome and uncomfortable for the patient. Given the risks of the hypoxia experienced as a result of sleep apnea, and the difficulty and discomfort associated with conventional testing for sleep apnea, it would be desirable to provide a relatively quick, inexpensive and non-invasive diagnostic tool for sleep apnea. Thus, a method for diagnosing sleep apnea solving the aforementioned problems is desired.

SUMMARY OF THE INVENTION

The method for diagnosing sleep apnea includes measuring concentrations of specific biomarkers in a biological sample from a patient. In order to determine whether a patient suffers from sleep apnea, or has a predisposition for developing sleep apnea, a biological sample from the patient is collected and then analyzed. The biological sample may include a sample of the patient's blood, saliva, urine, stool, or a combination thereof. If one or more of the following biomarker concentrations are found in the patient's sample, then the patient may be diagnosed as suffering from sleep apnea or having a predisposition for developing sleep apnea: between approximately 992.8 pg/mL and approximately 1309.6 pg/mL of adipsin; between approximately 1,640 pg/mL and approximately 2,900 pg/mL of betatrophin; between approximately 8,090.82 pg/mL and approximately 11,829.07 pg/mL of brain-derived neurotrophic factor (BDNF); between approximately 11.82 pg/mL and approximately 88.26 pg/mL of interleukin-13 (IL-13); between approximately 49.45 pg/mL and approximately 103.29 pg/mL of tumor necrosis factor-$\alpha$ (TNF-$\alpha$); and between approximately 16.55 pg/mL and approximately 29.76 pg/mL of the protein encoded by Human DNAJC27.

These and other features of the present invention will become readily apparent upon further review of the following specification.

DETAILED DESCRIPTION OF THE PREFERRED EMBODIMENTS

The method for diagnosing sleep apnea is a diagnostic method based on measuring concentrations of specific biomarkers in a sample from a patient. In order to determine whether a patient suffers from sleep apnea, or has a predisposition for developing sleep apnea, a sample from the patient is collected and then analyzed. The biological sample may include at least one of a blood sample, a saliva sample, a urine sample, and a stool sample. The analysis may be performed by enzyme linked immunosorbent assay (ELISA) kits or the like. A reduced level of adipsin in the sample can be indicative of sleep apnea. An elevated level of betatrophin, brain-derived neurotrophic factor (BDNP), interleukin-13 (IL-13), and/or tumor necrosis factor-$\alpha$ (TNF-$\alpha$) in the sample can be indicative of sleep apnea. For example, if one or more of the following biomarker concentrations are found in the patient's biological sample, then the patient may be diagnosed as suffering from sleep apnea or having a predisposition for developing sleep apnea: between approximately 992.8 pg/mL and approximately 1309.6 pg/mL of adipsin; between approximately 1,640 pg/mL and approximately 2,900 pg/mL of betatrophin; between approximately 8,090.82 pg/mL and approximately 11,829.07 pg/mL of brain-derived neurotrophic factor (BDNF); between approximately 11.82 pg/mL and approximately 88.26 pg/mL of interleukin-13 (IL-13); between approximately 49.45 pg/mL and approximately 103.29 pg/mL of tumor necrosis factor-$\alpha$ (TNF-$\alpha$); and between approximately 16.55 pg/mL and approximately 29.76 pg/mL of the protein encoded by Human DNAJC27.

The concentrations of the biomarkers in the patient's biological sample may be measured by any suitable technique, such as, for example, spectrographic analysis, chemical reagents or the like, as are well known in the field of bodily fluid analysis. Further, with regard to measuring levels of the protein encoded by Human DNAJC27, it should be understood that any suitable method for measuring concentrations of protein markers in blood plasma or serum may be used, such as conventional enzyme linked immunosorbent assay (ELISA) kits or the like.

In order to determine the above concentrations, concentrations of these biomarkers were measured in patients known to be suffering from sleep apnea and compared against measured concentrations from a control group of people without sleep apnea. Table 1 below summarizes these results, showing the concentration ranges of each biomarker (measured in picograms per milliliter) for the control group, for the patients with sleep apnea measured before surgical treatment for the sleep apnea, and for the patients with sleep apnea measured after surgical treatment.

TABLE 1

Comparison of Biomarker Concentrations in Patient Blood Samples

| Biomarker | Control Concentration (pg/mL) | Pre-Treatment Concentration (pg/mL) | Post-Treatment Concentration (pg/mL) |
| --- | --- | --- | --- |
| Adipsin | 1,309.6-4,115.2 | 992.8-2,384.0 | 1,290.4-4,889.6 |
| Betatrophin | 680.0-1,640.0 | 740.0-2,900.0 | 580.0-2,160.0 |
| BDNF | 3,530.75-8,090.82 | 3,502.88-11,829.07 | 2,714.2-11,954.5 |
| IL-13 | 3.5-11.82 | 2.7-88.26 | 3.1-26.51 |
| TNF-α | 12.83-49.45 | 13.99-103.29 | 12.25-84.95 |
| Protein (DNAJC27) | 0.55-16.55 | 1.76-29.76 | 2.24-26.55 |

Based on the data provided in Table 1, it can be seen that concentrations of between approximately 992.8 pg/mL and approximately 1309.6 pg/mL of adipsin; between approximately 1,640 pg/mL and approximately 2,900 pg/mL of betatrophin; between approximately 8,090.82 pg/mL and approximately 11,829.07 pg/mL of brain-derived neurotrophic factor (BDNF); between approximately 11.82 pg/mL and approximately 88.26 pg/mL of interleukin-13 (IL-13); between approximately 49.45 pg/mL and approximately 103.29 pg/mL of tumor necrosis factor-α (TNF-α); and between approximately 16.55 pg/mL and approximately 29.76 pg/mL of the protein encoded by Human DNAJC27 lie outside of the respective ranges of these biomarkers in the control group. Thus, these ranges of concentrations provide an indication for a diagnosis of sleep apnea or for a propensity to develop sleep apnea.

It is to be understood that the present invention is not limited to the embodiments described above, but encompasses any and all embodiments within the scope of the following claims.

I claim:

1. A method for diagnosing sleep apnea, comprising the steps of:
    collecting a biological sample from a patient;
    analyzing the biological sample to determine a concentration of a first biomarker and a second biomarker; and
    diagnosing the patient as having sleep apnea if a reduced level of the first biomarker is detected in the blood sample and/or an elevated level of the second biomarker is detected in the blood sample,
    wherein the first biomarker is adipsin and the second biomarker is betatrophin.

2. The method for diagnosing sleep apnea as recited in claim 1, wherein:
    a reduced level of adipsin includes concentrations of between approximately 992.8 pg/mL and approximately 1309.6 pg/mL; and/or
    an increased level of betatrophin includes concentrations of between approximately 1,640 pg/mL and approximately 2,900 pg/mL.

3. The method for diagnosing sleep apnea as recited in claim 1, wherein the step of collecting the biological sample from the patient comprises collecting a biological sample selected from the group consisting of a blood sample, a urine sample, a stool sample, a saliva sample and combinations thereof.

* * * * *